US006565518B2

(12) United States Patent
Blazey et al.

(10) Patent No.: US 6,565,518 B2
(45) Date of Patent: May 20, 2003

(54) TECHNIQUE FOR DIAGNOSING ATTENTION DEFICIT HYPERACTIVITY DISORDER

(75) Inventors: Richard N. Blazey, Penfield, NY (US);
Peter A. Parks, Topeka, KS (US);
David L. Patton, Webster, NY (US);
Paige Miller, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 20 days.

(21) Appl. No.: 09/865,902

(22) Filed: May 25, 2001

(65) Prior Publication Data

US 2003/0028121 A1 Feb. 6, 2003

(51) Int. Cl.[7] ................................................. A61B 5/00
(52) U.S. Cl. ........................ 600/549; 600/544; 600/546
(58) Field of Search ............................. 600/26–28, 300, 600/549, 558, 544, 546, 481, 500, 509; 128/897, 898

(56) References Cited

U.S. PATENT DOCUMENTS

| | | | | |
|---|---|---|---|---|
| 4,456,347 A | | 6/1984 | Stahly | 351/158 |
| 5,377,100 A | | 12/1994 | Pope et al. | 600/545 |
| 5,725,472 A | * | 3/1998 | Weathers | 600/21 |
| 5,913,310 A | | 6/1999 | Brown | 128/897 |
| 5,918,603 A | | 7/1999 | Brown | 128/897 |
| 5,940,801 A | | 8/1999 | Brown | 705/2 |
| 5,947,908 A | * | 9/1999 | Morris | 600/484 |
| 6,053,739 A | | 4/2000 | Stewart et al. | 434/236 |
| 6,097,980 A | | 8/2000 | Monastra et al. | 600/544 |
| 6,117,075 A | | 9/2000 | Barnes | 600/300 |
| 6,325,763 B1 | * | 12/2001 | Pfeiffer et al. | 600/549 |

OTHER PUBLICATIONS

Disclosure on the Development of EEG Diagnostics and Biofeedback for Attention–Deficit/Hyperactivity Disorders, Joel F. Lubar, Biofeedback and Self–Regulation, vol. 6, No. 3, 1991.

Functional Deficits in Basal Ganglia of Children with Attention–Deficit/Hyperactivity Disorder Shown with Functional Magnetic Resonance Imaging Relaxometry, Teichler et al., Nature Magazine, Apr. 2000, vol. 6, No. 4, pp 470–473.

Human Factors and Cognitive/Perceptual Information Processing, A virtuality Reality Environment for the Assessment of Attention Deficit Disorders in Children, Rizzo et al., Human Factors and Cognitive/Perceptual Information Processing, University of Southern California, Jul. 1999.

Clinical Practice Guideline: Diagnosis and Evaluation of the Child with Attention–Deficit/Hyperactivity Disorder, Homer et al., American Academy of Pediatrics May 2000.

* cited by examiner

Primary Examiner—Max F. Hindenburg
Assistant Examiner—Charles Marmor, II
(74) Attorney, Agent, or Firm—William F. Noval

(57) ABSTRACT

A method for determining a threshold value of a parameter used to determine whether an individual has Attention Deficit Hyperactivity Disorder (ADHD). The method includes: providing a group of individuals a segment of which is known to have ADHD and a segment of which is known to be normal and not have ADHD; testing each individual in the group by sampling the peripheral skin temperature of the individual during a pre-determined time interval when the individual is in an inactive state to provide sampled peripheral skin temperature data, and analyzing the sampled peripheral skin data to produce a parameter value for that individual. The method further includes: processing the individual parameter values for all of the members of the group to determine a threshold parameter value which is acceptable for determining whether or not an individual has ADHD when tested by the testing procedure.

29 Claims, 4 Drawing Sheets

TECHNIQUE FOR DIAGNOSING ATTENTION DEFICIT HYPERACTIVITY DISORDER

FIELD OF THE INVENTION

This invention relates in general to a technique for diagnosing Attention Deficit Hyperactivity Disorder (ADHD) and more particularly to a technique for measuring an individual's peripheral temperature to determine values indicative of ADHD.

BACKGROUND OF THE INVENTION

ADHD is the most common neurobehavioral disorder of childhood as well as among the most prevalent health conditions affecting school-aged children. Between 4% and 12% of school age children (several millions) are affected. $3 billion is spent annually on behalf of students with ADHD. Moreover, in the general population, 9.2% of males and 2.9% of females are found to have behavior consistent with ADHD. Upwards of 10 million adults may be affected.

ADHD is a difficult disorder to diagnose. The core symptoms of ADHD in children include inattention, hyperactivity, and impulsivity. ADHD children may experience significant functional problems, such as school difficulties, academic underachievement, poor relationships with family and peers, and low self-esteem. Adults with ADHD often have a history of losing jobs, impulsive actions, substance abuse, and broken marriages. ADHD often goes undiagnosed if not caught at an early age and affects many adults who may not be aware of the condition. ADHD has many look-alike causes (family situations, motivations) and co-morbid conditions (depression, anxiety, and learning disabilities) are common.

Diagnosis of ADHD involves a process of elimination using written and verbal assessment instruments. However, there is no one objective, independently validated test for ADHD. Various objective techniques have been proposed but have not yet attained widespread acceptance. These include:

1. The eye problem called convergence insufficiency was found to be three times more common in children with ADHD than in other children by University of California, San Diego researchers.
2. Infrared tracking to measure difficult-to-detect movements of children during attention tests combined with functional MRI imaging of the brain were used by psychiatrists at McLean Hospital in Belmont, Mass. to diagnose ADHD in a small group of children (*Nature Medicine*, Vol. 6, No. 4, April 2000, Pages 470–473).
3. Techniques based on EEG biofeedback for the diagnoses and treatment of ADHD are described by Lubar (*Biofeedback and Self-Regulation*, Vol. 16, No. 3, 1991, Pages 201–225).
4. U.S. Pat. No. 6,097,980, issued Aug. 1, 2000, inventor Monastra et al, discloses a quantitative electroencephalographic process assessing ADHD.
5. U.S. Pat. No. 5,913,310, issued Jun. 22, 1999, inventor Brown, discloses a video game for the diagnosis and treatment of ADHD.
6. U.S. Pat. No. 5,918,603, issued Jul. 6, 1999, inventor Brown, discloses a video game for the diagnosis and treatment of ADHD.
7. U.S. Pat. No. 5,940,801, issued Aug. 17, 1999, inventor Brown, discloses a microprocessor such as a video game for the diagnosis and treatment of ADHD.
8. U.S. Pat. No. 5,377,100, issued Dec. 27, 1994, inventors Pope et al., discloses a method of using a video game coupled with brain wave detection to treat patients with ADHD.
9. Dr. Albert Rizzo of the Integrated Media Systems Center of the University of Southern California has used Virtual Reality techniques for the detection and treatment of ADHD.
10. U.S. Pat. No. 6,053,739, inventors Stewart et al., discloses a method of using a visual display, colored visual word targets and colored visual response targets to administer an attention performance test.

U.S. Pat. No. 5,377,100, issued Dec. 27, 1994, inventors Patton et al., discloses a system and of managing the psychological state of an individual using images.

U.S. Pat. No. 6,117,075 Barnea discloses a method of measuring the depth of anesthesia by detecting the suppression of peripheral temperature variability.

There are several clinical biofeedback and physiologic monitoring systems (e.g. Multi Trace, Bio Integrator). These systems are used by professional clinicians. Although skin temperature spectral characteristics have been shown to indicate stress-related changes of peripheral vasomotor activity in normal subjects, there has been no disclosure of use of variations in skin-temperature response to assist in diagnosing ADHD. (See: Biofeedback and Self-Regulation, Vol. 20, No. 4, 1995).

As discussed above, the primary method for diagnosing ADHD is the use of a bank of written and verbal assessment instruments designed to assess criteria established by American Medical Association (AMA) as described in the Diagnostic and Statistics manual (DSM-IV) and administered by the school psychologist or other licensed practitioner. In some cases those individuals who meet DSM-IV criteria for ADHD diagnosis are prescribed a drug such as Ritalin. Behavioral observations of the patient while on Ritalin are conducted to assess the impact of prescribed medication.

There is thus a need for a simple, inexpensive, and reliable technique for assisting in the diagnosis of ADHD.

SUMMARY OF THE INVENTION

According to the present invention, there is provided a solution to the problems and fulfillment of the needs discussed above.

According to a feature of the present invention, there is provided a method of determining whether an individual has Attention Deficit Hyperactivity Disorder (ADHD) comprising:

sampling the peripheral skin temperature of a human subject during a predetermined time interval when the subject is in an inactive state to provide a sampled peripheral skin temperature data and analyzing the peripheral skin temperature data for a pre-selected parameter, to determine whether said pre-selected parameter has a value indicative of ADHD.

ADVANTAGEOUS EFFECT OF THE INVENTION

The invention has the following advantages.

1. A technique for diagnosing ADHD is provided which is simple, inexpensive and reliable.

DETAILED DESCRIPTION OF THE INVENTION

According to the invention, it has been found that a signature of ADHD is hidden in fluctuation of the temperature of the skin as measured at the extremities such as at a fingertip. It is well known in the art that as a person's stress level increases the blood vessels in the body constrict (as is evidenced by the fact that a person's blood pressure increases as their level of stress increases). As the blood vessels in the body constrict, blood flow is restricted. This is most evident in the extremities such as the fingers, because the blood vessels in the extremities are small and furthest from the heart. A direct result of decreased blood flow to the blood vessels in the extremities is a decrease in the peripheral temperature of the extremities. Conversely, as a person's stress level decreases and one relaxes the blood vessels also relax and dilate causing blood flow to increase. As the blood flow to the vessels in the extremities increases, the peripheral temperature of the extremities increases. When a subject with ADHD is subjected to sensory deprivation such as being made to look at a blank screen or an obscured image, the lack of stimulation increases and their level of anxiety and their stress level increases. As their stress level increases their blood constrict and the peripheral temperature of their extremities decreases. Biofeedback practitioners have long used measurement of hand temperature to help subjects manage their physiology by controlling blood flow to the extremities. The literature reports that reduced blood flow to the brain is frequently found in patients with ADHD.

In addition to peripheral skin temperature and peripheral skin temperature variability there are other physiologic measures which are known (or potential) indicators of stress such as; bilateral temperature variability, heart rate, heart rate variability, muscle tension (excessive and chronic measured via surface electromyography—sEMG), bilateral muscle tension imbalance, galvanic skin response (i.e., electro dermal response—EDR), eye saccades, blood oxygen ($SpO_2$), salivary IGA, electroencephalography (EEG), peripheral blood flow (measured via photoplethismography—PPG), and peripheral blood flow variability (PPG).

Figure 1:
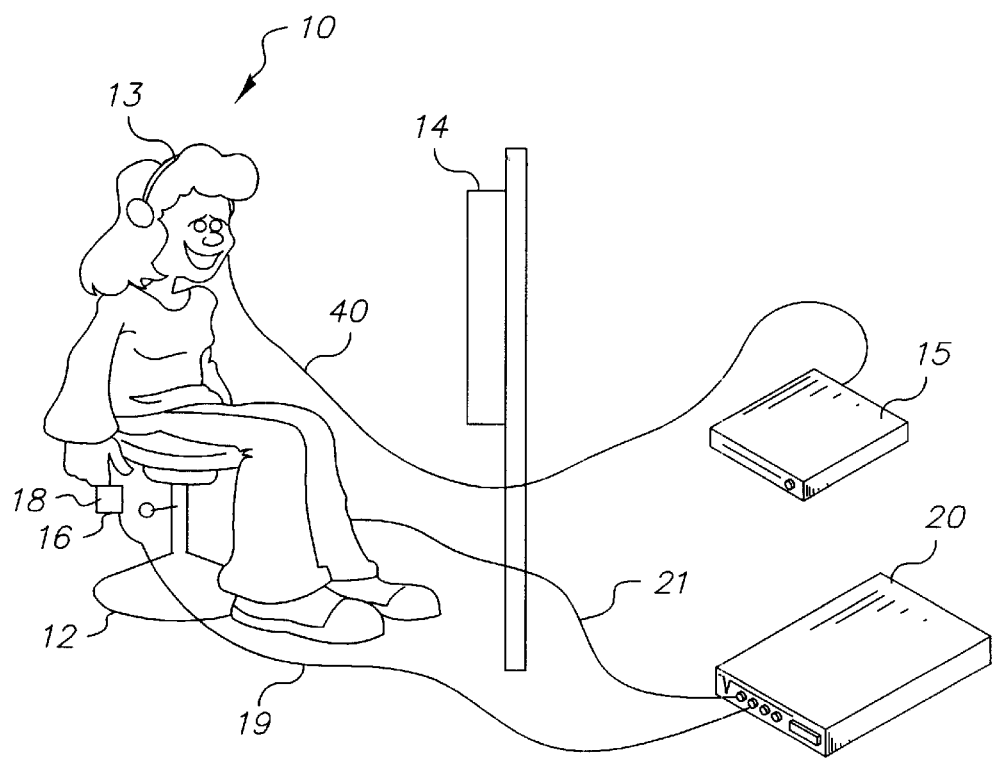
FIG. 1 is a diagrammatic view illustrating an embodiment of the present invention.

As shown in FIG. 1, a subject 10 is sitting on a chair 12 watching a screen 14. The subject is at rest in an inactive state. The subject 10 is shown wearing a set of earphones 13 connected via a wire 40 to a sound generating device 15. The earphones 13 may be used to reduce or eliminate the audio stimulus from the environment during the test. The method described in this embodiment of the present invention places the subject in sensory deprived surroundings. Other examples of providing sensory deprivation are to have the subject wear a pair of translucent glasses, goggles or eye mask (not shown). The glasses or goggles block any visual stimulus from the subject 10. A sensor 18 measures the temperature of a fingertip 16 of subject 10. The temperature readings are supplied to module 20 via a wire 19. The temperature can be taken from one hand or both hands and from one or more fingers on each hand. The temperature sensor for the other hand is not shown but is connected via wire 21 to module 20.

Figure 2:
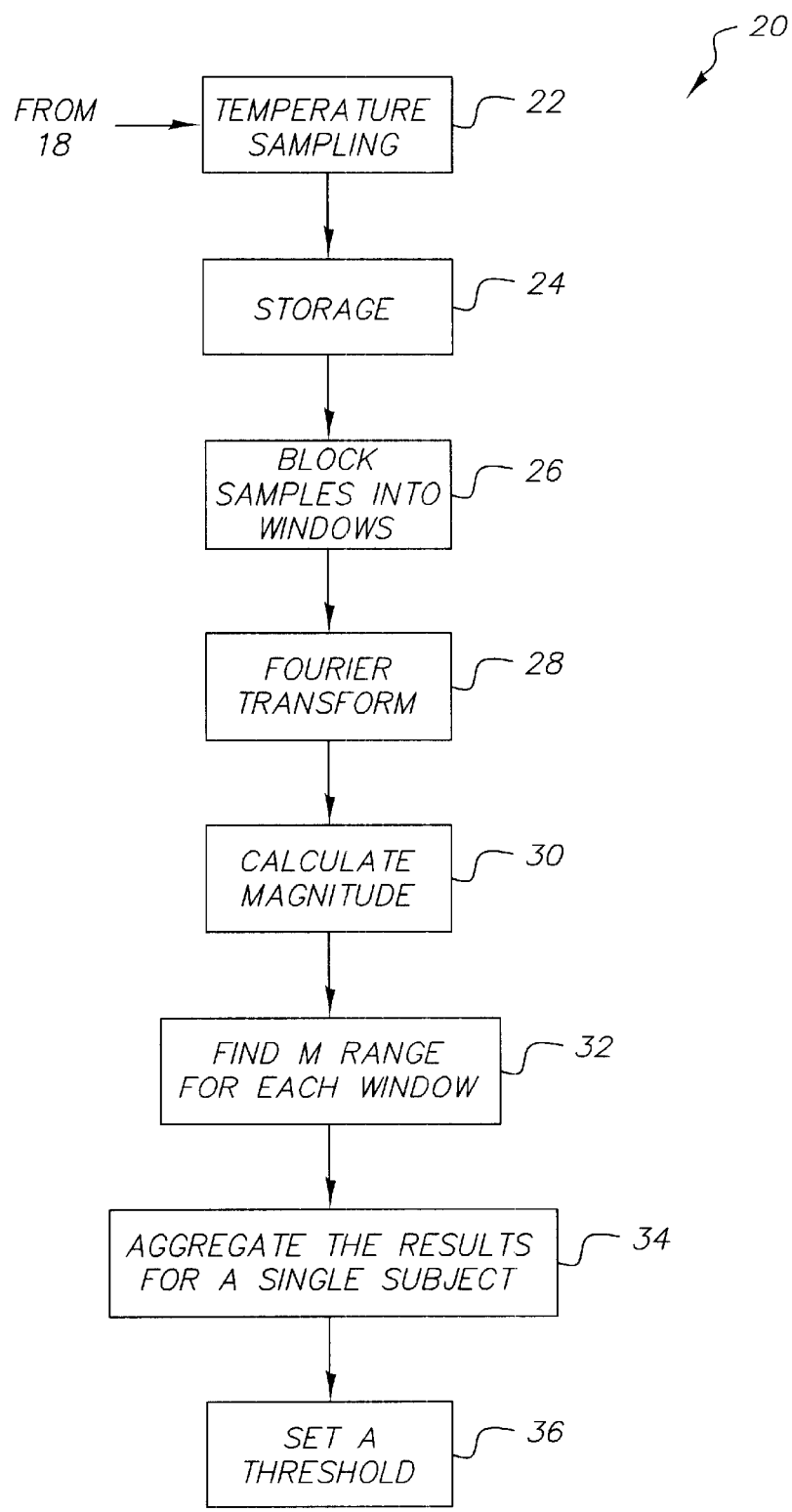
FIG. 2 is a block diagram of a system incorporating the present invention.

As shown in FIG. 2, module 20 includes temperature sampling circuit 22, data storage 24, window blocking 26, Fourier transform 28, Magnitude calculation 30, M range calculation 32, aggregation step 34 and Thresholding step 36.

In FIG. 1, the fingertip temperature is first recorded during an interval when the subject 10 has been asked to sit quietly for a period of about ten minutes. The temperature data is sampled 22 at a time interval $\Delta t$ creating a list of n temperature samples, which are stored in storage 24.

Now referring to FIG. 2, in block 26, the n samples are divided into groups of m samples, each group corresponding to a given time window of width $\Delta t$(~32–64 sec) equally spaced in time (~50 sec) across the entire data collection time interval $\Delta t$. The data from each window is then passed through a Fast Fourier Transform (FFT) algorithm producing $2^{m-1}$ data points spaced equally in frequency space. The values are complex numbers having form $$FFT(f_m) = A(f_m) + B(f_m)i$$

where i is the $\sqrt{-1}$. The Phase $\Phi(f_m)$ is then found from the equation $$\Phi_l(f_m) = \text{Tan}^{-1}\left(\frac{B(f_m)}{A(f_m)}\right) \quad (1.0)$$

and the Magnitude $M(f_m)$ from $$M_l(f_m) = \sqrt{B(f_m)^2 + A(f_m)^2} \quad (1.1)$$

Figure 3:
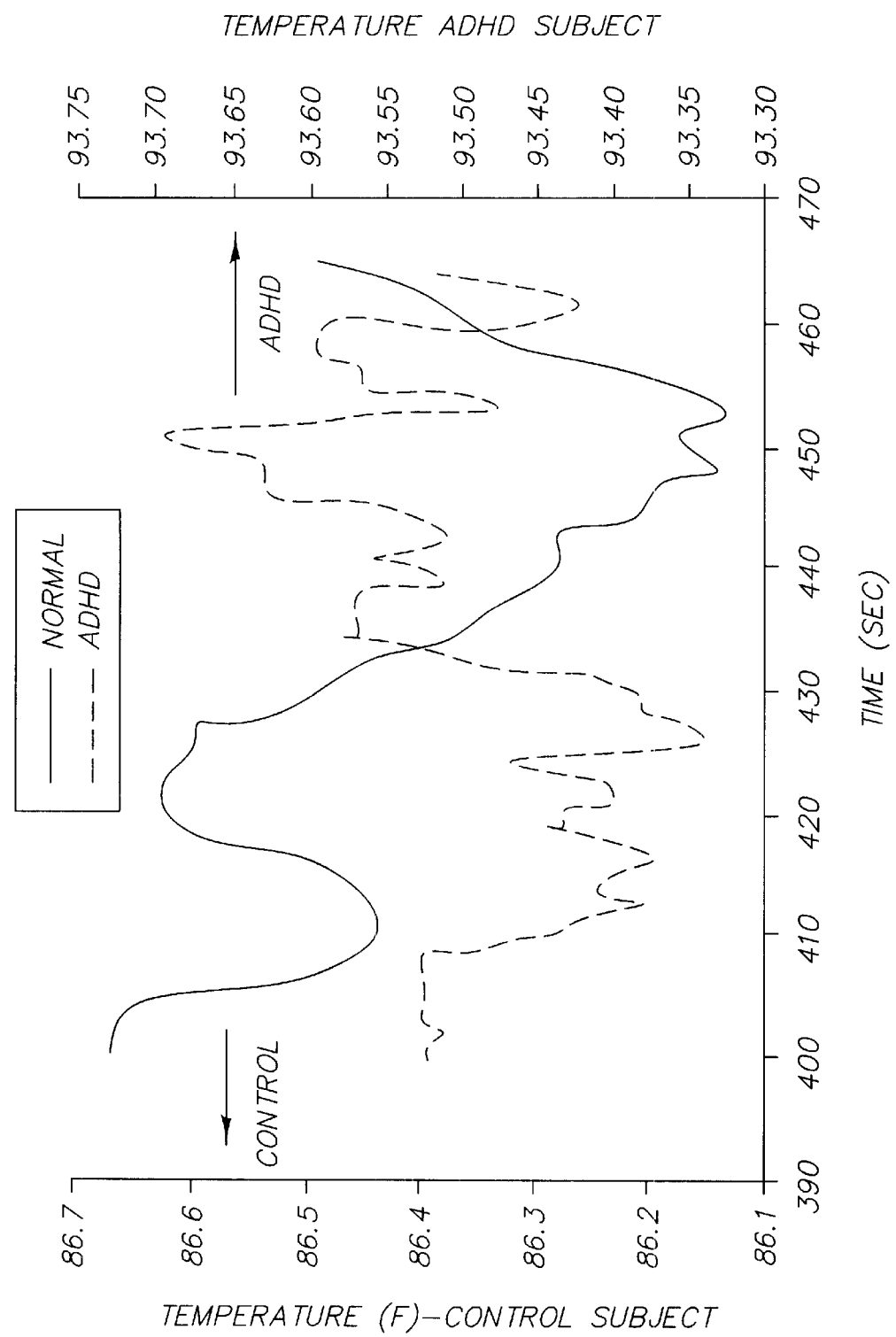
FIGS. 3, 4a and 4b are graphical views useful in explaining the present invention.

In the equations 1.0 and 1.1 the subscript l refers to the fact that a separate signal is extracted for each hand so the subscript is l for data extracted from the left-hand data and r for data from the right hand. FIG. 3 graphically illustrates the temperature signal during one window for a normal subject and a person diagnosed with ADHD.

Figure 4A:
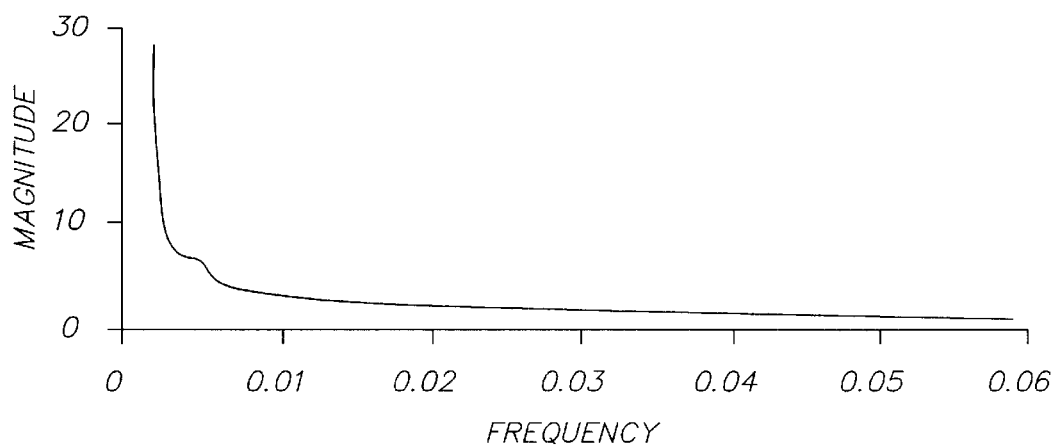
Figure 4B:
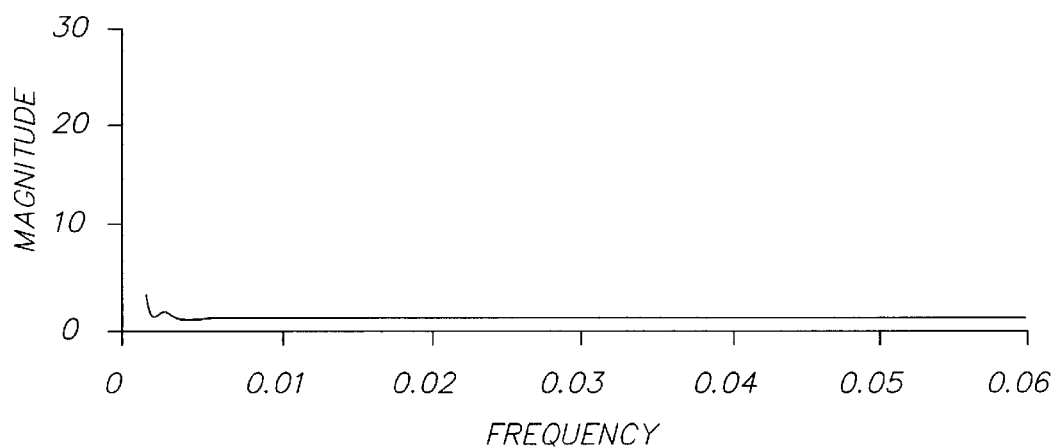

FIGS. 4a and 4b graphically illustrate the magnitude transform for the data corresponding with a subject with ADHD and a normal subject. The magnitude spectrum undergoes dramatic changes essentially changing from a hyperbolic curve to a flat response.

Referring again to FIG. 2.

Raw Data

The raw data $T_{k,l}(t)$ is the temperature taken from hand l at a fingertip 16 as shown in FIG. 1, during the 10-minute session. The sessions were taken over a period of weeks. Some subjects had as few as 2 sessions and some as many as 5 sessions. k is used to represent the session.

Windows

The data for each session were divided into a series of windows (step 26) prior to performing the Fourier Transform operation 28. Call the window width w. In this analysis, the window width was 64 seconds and there were 10 windows spaced at 50-second intervals (the windows overlap) across the 600 sec baseline spanning the range of 100–500 sec, other values of w can be used. The window number in a session is referred to with the letter j. For each window a FFT algorithm calculates the Fourier Transform F(f). The Magnitude and Phase of this transform are defined as given above.

In step 32 the range of magnitude variation during a window is calculated using equation (1.2) below where $f_{max}$ and $f_{min}$ are the frequencies where the Magnitude is the greatest and the least respectively (note the dc component at frequency zero is excluded).

$$M_{range} = [M(f_{max}) - M(f_{min})] \quad (1.2)$$

In a further embodiment of this method, other statistics from a Fourier Transform, calculated from the quantities denoted above as $A(f_m)$, $B(f_m)$, $\Phi(f_m)$, and $M(f_m)$ can be used. In addition to using Fourier Transforms, this further embodiment can use statistics derived from a Wavelet transform of the data or other filtering of the data (as in Strang, G. and Nguyen, T. (1996), *Wavelets and Filter Banks*, Wellesley-Cambridge Press, Wellesley, Me.).

Aggregation of Samples

Samples are aggregated in step 34. There are 10 samples from each hand from each session. The first step is to choose an aggregation statistic, which can be the mean, median, variance, or other statistic, which is an aggregate of the computed $M_{range}$ values in each window for each session and each hand. Other statistics that can be used for aggregation include the standard deviation, range, interquartile distance, skewness, kurtosis, Winsorized mean and variance, and robust estimates of mean and variance. Equations below are given for aggregating the mean and the variance. The mean magnitude range for the left hand of session k is found from equation 2.0 where z is the number of windows in the session.

$$\langle M_{k,l} \rangle = \frac{\sum_{j=1}^{z} [M(f_{\max})_j - M(f_{\min})_j]}{z} \quad (2.0)$$

And the corresponding variance is:

$$\langle Var_{k,l} \rangle = \frac{\sum_{j=1}^{z} \{[M(f_{\max})_{j,l} - M(f_{\min})_{j,l}] - \langle M_{k,l} \rangle\}^2}{z} \quad (2.1)$$

Combining these session means and variances over both hands and all the sessions s that a subject attended gives an aggregated mean $\mu$ and aggregated variance $var_i$.

$$\mu = \frac{\sum_{k=1}^{s} \sum_{l=1}^{2} \langle M_{k,l} \rangle}{2s} \quad (2.2)$$

$$\langle var \rangle = \frac{\sum_{k=1}^{s} \sum_{l=1}^{2} \langle var_{k,l} \rangle}{2s} \quad (2.3)$$

Other embodiments of this aggregation step include using the data from only one hand—either the left hand, the right hand, or the dominant hand and if the subject is ambidextrous, the dominant hand would be defined as the average of both hands. In addition, these embodiments may not require averaging of several sessions, but selecting only one session for use or using a weighted combination of each session's results.

Thus, the totality of these embodiments include methods that involve any and all combinations of: statistics derived from Fourier or Wavelet transformations or other filtering, plus any one of many possible aggregation statistics, plus using data from only one hand or the dominant hand or the average of both hands, plus using either all sessions or a subset of the sessions or a weighted combination of each session's results.

Diagnostic Indicator

A Diagnostic indicator is determined by setting a threshold level $\theta$ for the aggregation statistic in step 36. When the subject's measured aggregate statistic is less than the threshold $\theta$, the test indicates the subject has ADHD. When the subject's measured aggregate statistic is greater than the threshold $\theta$ the test indicates the subject does not have ADHD. A single threshold may be used for all subjects or the threshold may be set differently for different groups such as gender or age.

The method of obtaining the threshold $\theta$ is now described. It is similar to a method in the statistical literature called "discriminant analysis". In fact, one could use discriminant analysis c for this data; however this method was devised because it can be enhanced and used for purposes discriminant analysis cannot handle. This enhancement will be described later.

Figure 5:
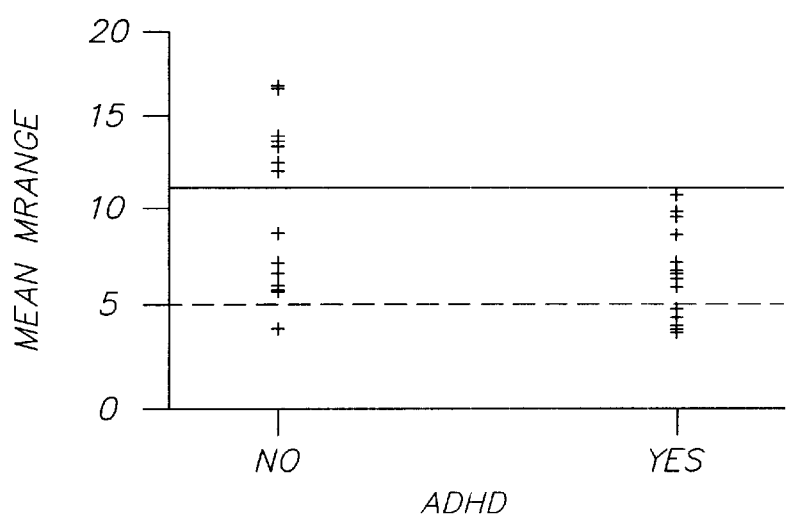
FIG. 5 is a diagram of an example of finding the proper threshold θ to separate ADHD subjects from non-ADHD subjects.

To find the value of $\theta$ that gives the highest percentage of correct diagnoses, a simple example must first be illustrated. In this example, there are 32 aggregation statistics, one for each subject in the study. Next thresholds $\theta=11.5$ and $\theta=5$ were considered. The 32 aggregation statistics are shown in FIG. 5, along with threshold $\theta=11.5$ as the solid line and $\theta=5$ as the dashed line. A different percent of correct diagnoses results when $\theta=11.5$ is used compared to $\theta=5$. Naturally, there are an infinite number of potential values for $\theta$, and a procedure to pick the one that gives the highest percent of correct diagnoses is needed.

Thus, the following procedure was used: Twenty-five equally spaced values, spanning the range of the 32 aggregation statistics, were found. At each of these 25 values, the percent p of correctly diagnosed subjects was computed. A spline is fitted through this data, so that p is now estimated as a smooth function of $\theta$. Then, the maximum value of this smooth function is found, and $\theta$ is set to be where the percent of correct diagnoses is maximized. Since this is often an interpolation, the value of the spine function at $\theta$ is not used, but instead is recomputed to percent of correct diagnoses at $\theta$.

An enhanced method that works in situations where discriminant analysis does not work calls for replacing the percent of correct diagnoses in the above procedure with a weighted percent of false positive and false negative diagnosis, an then to minimize this weighted percent. This method allows the flexibility to choose the relative importance of false positive and false negatives, and to have this used in determining $\theta$. One way to set the relative importance is to use the cost of a false negative diagnosis.

Virtually every analysis method tried produced correct diagnoses at a rate that is statistically above chance results at the $\alpha=0.05$ level, and many methods produced statistically significant results at the $\alpha=0.01$ level (see Table 1 through Table 8). This indicates that the diagnosis method proposed, using windowed Fourier transforms of hand temperatures, has found a real effect. The diagnosis obtained are significantly better than one would obtain using random chance.

For example, comparing the case where the variance was used on all data with one threshold for everyone, we see the method produces 68.8% correct diagnoses. If the variance is used with gender thresholds, the percent correct increases to 84.4%. Using different thresholds by gender improves the diagnoses, see Table 1. This is consistent with statements by Raymond, K. B. (1997). *Dissertation Abstracts International*: Section A: Humanities and Social Sciences, 57 (12-A) 5052, and also Katz, L., Goldstein, G., Geckle, M. (1998). Journal of Attention Disorders. 2(4), 239–47, who state that females with ADHD are under-diagnosed. This suggests that a different standard of diagnosis is necessary for females. Age based thresholds improve the percent correct by 3% (see Table 1). Any of the methods of separating thresholds by gender or age or neither, produce diagnoses that are statistically better than chance.

Another result shown in tables, reveals that removing noises (as described below) produce the highest percent correct diagnosis. This is consistent with the fact, that the data removed was contaminated and less likely to demonstrate the effect of interest. Further, note that without using gender or age thresholds, the variance produces correct diagnoses 84.6% of the time. Using gender or age thresholds, or using the mean or median, did not improve the results.

Listed below are the types of noise:

Self Diversion
    Children divert themselves by moving, using mental exercises or external tools such as gum or suckers External Stimulation
    Noises, Room Temperature, Parents in Room etc.

Technical Problems
    Loose sensors, missing sensors, pauses, computer failures Sleep problems
    Child falls asleep during the session.

Medication Problems
    Child's medication is still active during session or child is on long acting drug Other analysis methods were tried and found to be less successful, though these methods were significantly better than chance. For example, applying a Butterworth filter to the temperature data as suggested by Shusterman, V. and Barnea, O. (1995). *Biofeedback and Self-Regulation*, 20(4), 357–365 did not produce improved results. Nor did separating the data by session (Table 7) or by hand (Table 8). The highest accuracy is obtained by averaging sessions and averaging two hands for tests. The benefit of using both sessions and both hands is that reduction of variability occurs, enabling more reliable diagnoses. A well-known statistical principle is that the variability of the average of multiple sessions or two hands is less than the variability of one session or one hand. Nor did removing the first two time periods (Tables 3, 4 and 6) improve the percent of correct diagnoses.

The percent of false positive and false negative diagnoses was examined. Using the mean statistic and one threshold for all subjects, a result of 25% false positive diagnoses and 0% false negative diagnoses was achieved. Using separate thresholds by gender and the variance statistic produced a result of 9.4% false positive diagnoses, and 6.3% false negative diagnoses.

The test method was applied to 50% ADHD subjects and 50% non-ADHD subjects; however, if it was applied only to symptomatics (a subset of the population in which most have ADHD), it is shown below that the method test actually will produce higher accuracy. The actual rate of false diagnoses depends on the assumed percent of true ADHD subjects in the population of symptomatics to be tested.

Let p be the proportion of subjects in the study who actually have ADHD. Let $f_+$ be the proportion of false positive diagnoses of those subjects who do not have ADHD. Let $f_+$ be the proportion of false negative diagnoses of those subjects who do have ADHD. Then the proportion c of correct diagnoses is:

$$c = 1 - (f_- p - f_+(1-p))$$

The derivative of c is:

$$\frac{\partial c}{\partial p} = f_+ - f_-$$

The derivative is positive whenever $f_+$ is greater than $f_-$. Thus, increasing the value of p will increase the proportion c of correct diagnoses.

The invention has been described in detail with particular reference to certain preferred embodiments thereof, but it will be understood that variations and modifications can be effected within the spirit and scope of the invention.

APPENDIX

The following is a list of tables in the Appendix that show the percent of subjects correctly diagnosed by different analysis methods, or by using different portions of the data, or by a combination of analysis methods and different portions of the data:

Table 1: All data used Table 2: Windows with technical problems (sensor falling off or pause button pushed) eliminated Table 3: First two time windows removed Table 4: Same as Table 2, but first two time windows are removed Table 5: Sessions where there were serious self-diversion problems were removed.

Table 6: Same as 5, but first two time periods were also removed.

Table 7: Same as 1, one threshold for all subjects, but data from only session 1, or only session 2 or both sessions were used.

Table 8: Same as 1, one threshold for all subjects, but data from left hand; or right hand; or dominant hand used.

TABLE 1

Percent of Correct Diagnoses

Subjects with medication problems removed (2822 & 2813 Session 1)
Both Hands/Both Sessions, N = 32
95% Significance is >65.6% correct, 99% Significance is >71.9% correct
Data used: All Data

| | Statistic Used: | | |
|---|---|---|---|
| | Mean % Correct Diagnoses | Median % Correct Diagnoses | Variance % Correct Diagnoses |
| Thresholds used | 75.00 | 68.75 | 68.75 |
| One Threshold for Everyone | | | |
| Age Thresholds | 78.13 | 71.88 | 71.88 |
| Gender Thresholds | 81.25 | 68.75 | 84.38 |

TABLE 2

Percent of Correct Diagnoses

Subjects with medication problems removed (2822 & 2813 Session 1)
Both Hands/Both Sessions, N = 32
95% Significance is >65.6% correct, 99% Significance is >71.9% correct
Data used: Remove technical problems

| | Statistic Used: | | |
|---|---|---|---|
| | Mean % Correct Diagnoses | Median % Correct Diagnoses | Variance % Correct Diagnoses |
| Thresholds used One Threshold for Everyone | 68.75 | 68.75 | 68.75 |
| Age Thresholds | 75.00 | 75.00 | 75.00 |
| Gender Thresholds | 78.13 | 68.75 | 81.25 |

TABLE 3

Percent of Correct Diagnoses

Subjects with medication problems removed
Both Hands/Both Sessions, N = 32
95% Significance is >65.6% correct, 99% Significance is >71.9% correct
Data used: Remove 1st 2 time periods

| | Statistic Used: | | |
|---|---|---|---|
| | Mean % Correct Diagnoses | Median % Correct Diagnoses | Variance % Correct Diagnoses |
| Thresholds used One Threshold for Everyone | 68.73 | 65.63 | 65.63 |
| Age Thresholds | 71.88 | 68.75 | 65.63 |
| Gender Thresholds | 71.88 | 65.63 | 68.75 |

TABLE 4

Percent of Correct Diagnoses

Subjects with medication problems removed
Both Hands/Both Sessions, N = 32
95% Significance is >65.6% correct, 99% Significance is >71.9% correct
Data used: Remove technical problems and 1st 2 time periods

| | Statistic Used: | | |
|---|---|---|---|
| | Mean % Correct Diagnoses | Median % Correct Diagnoses | Variance % Correct Diagnoses |
| Thresholds used One Threshold for Everyone | 65.63 | 65.63 | 68.75 |
| Age Thresholds | 71.88 | 68.75 | 68.75 |
| Gender Thresholds | 68.75 | 65.63 | 71.88 |

TABLE 5

Percent of Correct Diagnoses

Subjects with medication problems removed (2822 & 2813 Session 1)
Both Hands/Both Sessions, N = 26
95% Significance is >65.4% correct, 99% Significance is >73.1% correct
Data used: Remove tech/external/self-diverted problems

| | Statistic Used: | | |
|---|---|---|---|
| | Mean % Correct Diagnoses | Median % Correct Diagnoses | Variance % Correct Diagnoses |
| Thresholds used One Threshold for Everyone | 76.92 | 73.08 | 84.62 |

TABLE 5-continued

Percent of Correct Diagnoses

Subjects with medication problems removed (2822 & 2813 Session 1)
Both Hands/Both Sessions, N = 26
95% Significance is >65.4% correct, 99% Significance is >73.1% correct
Data used: Remove tech/external/self-diverted problems

| | Statistic Used: | | |
|---|---|---|---|
| | Mean % Correct Diagnoses | Median % Correct Diagnoses | Variance % Correct Diagnoses |
| Age Thresholds | 84.62 | 76.92 | 84.62 |
| Gender Thresholds | 76.92 | 76.92 | 84.62 |

TABLE 6

Percent of Correct Diagnoses

Subjects with medication problems removed (2822 & 2813 Session 1)
Both Hands/Both Sessions, N = 32
95% Significance is >65.4% correct, 99% Significance is >73.1% correct
Data used: Remove tech/external/self-diverted problems and 1st 2 time pds

| | Statistic Used: | | |
|---|---|---|---|
| | Mean % Correct Diagnoses | Median % Correct Diagnoses | Variance % Correct Diagnoses |
| Thresholds used One Threshold for Everyone | 73.08 | 65.38 | 73.08 |
| Age Thresholds | 80.77 | 76.92 | 76.92 |
| Gender Thresholds | 69.23 | 73.08 | 76.92 |

TABLE 7

Percent of Correct Diagnoses by Session

Subjects with medication problems removed (2822 & 2813 Session 1)
Data used: All Data

| | Statistic Used: | | |
|---|---|---|---|
| | Mean % Correct Diagnoses | Median % Correct Diagnoses | Variance % Correct Diagnoses |
| Session Used Session 1 | 68.75 | 68.75 | 71.88 |
| Session 2 | 71.88 | 65.63 | 68.75 |
| Both Sessions | 75.00 | 68.75 | 68.75 |

TABLE 8

Percent of Correct Diagnoses by Session

Subjects with medication problems removed (2822 & 2813 Session 1)
Data used: All Data

| | Statistic Used: | | |
|---|---|---|---|
| | Mean % Correct Diagnoses | Median % Correct Diagnoses | Variance % Correct Diagnoses |
| Hand Used Both Hands | 75.00 | 68.75 | 68.75 |
| Dominant Hand | 75.00 | 65.63 | 65.63 |
| Left Hand | 65.63 | 62.50 | 71.88 |
| Right Hand | 65.63 | 68.75 | 68.75 |

What is claimed is:

1. A method for determining a threshold value of a parameter used to determine whether an individual has Attention Deficit Hyperactivity Disorder (ADHD) comprising:
   providing a group of individuals a segment of which is known to have ADHD and a segment of which is known to be normal and not have ADHD;
   testing each individual in the group by sampling the peripheral skin temperature of the individual during a predetermined time interval when the individual is in an inactive state to provide sampled peripheral skin temperature data, and analyzing the sampled peripheral skin data to produce a parameter value for that individual; and
   processing the individual parameter values for all of the members of the group to determine a threshold parameter value, which is acceptable for determining whether or not an individual has ADHD when tested by said testing.

2. The method of claim 1 wherein said processing uses discriminant analysis to determine said acceptable threshold parameter value.

3. The method of claim 1 wherein said processing uses a selected percent of correct diagnoses to determine said acceptable threshold parameter value.

4. The method of claim 1 wherein said processing uses a selected weighted percent of false positive and/or false negative diagnoses to determine said acceptable threshold parameter value.

5. The method of claim 1 wherein said group of individuals provided include individuals of female gender and individuals of male gender in each said segment, and
   wherein an acceptable threshold parameter value is determined for one or both of said genders.

6. The method of claim 1 wherein said group of individuals provided include individuals in at least two different age groups in each said segment; and
   wherein an acceptable threshold parameter value is determined for one or more of said different age groups.

7. The method of claim 1 wherein in said testing the peripheral skin temperature of at least one hand of each individual is sampled.

8. The method of claim 1 wherein in said testing, the peripheral temperature of the dominant hand of each individual is tested.

9. The method of claim 7 wherein the peripheral skin temperature of both hands of each individual is sampled and said parameter value for that individual is produced by analyzing the sampled peripheral skin data from both said hands.

10. The method of claim 1 wherein prior to testing each individual if, one or more of the following noises are present it is minimized, self diversion, external stimulation, technical problems, sleep problems, medication problems.

11. A method of claim 1 including providing an earphone to be worn by the individual during said predetermined time interval to block out ambient noise or to receive white noise to reduce or eliminate audio stimulus from the ambient environment during said time interval.

12. The method of claim 11 including providing a source of white noise to be coupled to said earphone to provide white noise during said predetermined time interval.

13. The method of claim 1 including providing glasses or goggles to be worn by the individual during said predetermined time interval to block out or eliminate ambient visual stimulus from the ambient environment during said time interval.

14. The method of claim 1 wherein in said testing one predetermined time interval is selected.

15. The method of claim 1 wherein in said testing a weighted combination of each predetermined time interval is selected.

16. A method of determining whether an individual has Attention Deficit Hyperactivity Disorder, comprising:
   sampling the peripheral skin temperature of an individual during a predetermined time interval when the individual is in an inactive state to provide sampled peripheral skin temperature data;
   dividing the data into a series of windows of equal time intervals across the pre-determined time interval;
   for each window applying a fast Fourier Transform algorithm (FFT) to produce a data set FFT magnitudes and determining a range of FFT magnitude variation, which is the difference between the FFT magnitude at a frequency $f_{max}$ and FFT magnitude at the minimum frequency $f_{min}$;
   aggregating the magnitude ranges for one of or less than all of the windows to produce an aggregate magnitude range value which is indicative of whether or not the individual has ADHD.

17. The method of claim 16 wherein said aggregate magnitude range value is the mean of said magnitude range values of all of said windows.

18. The method of claim 16 wherein said aggregate magnitude range value is the median of said magnitude range values of all of said windows.

19. The method of claim 16 wherein said aggregate magnitude range value is the variance of said magnitude range values of all of said windows.

20. The method of claim 16 wherein said aggregate magnitude range value is determined by an aggregation statistical algorithm of said magnitude range values of all of said windows.

21. The method of claim 16 wherein said sampling includes sampling the peripheral skin temperature of said individual during two or more pre-determined time intervals, wherein said aggregate magnitude range value is aggregated for one or more of said pre-determined time intervals.

22. The method of claim 16 wherein said sampling includes sampling the peripheral skin temperature of one or both hands of said individual, and wherein said aggregate for said one or said both hands.

23. The method of claim 16 wherein said the magnitude range of one or more windows at the beginning of said pre-determined time interval is not used to produce said aggregate range value.

24. The method of claim 16 wherein prior to said sampling, if one or more of the following noises are present it is minimized, self diversion, external stimulation, technical problems, sleep problems, medication problems.

25. The method of claim 16 wherein in said aggregating the magnitude range one or more of the following are used;
   the standard deviation, range, interquartile distance, skewness, kurtosis, Winsorized mean and variance, and robust estimates of mean and variance.

26. The method of claim 16 wherein in said aggregating the magnitude range;
   the data from only one hand is used.

27. The method of claim 26 wherein said one hand is one of the left hand, the right hand or the dominant hand.

28. A method for determining a threshold value of a parameter used to determine whether an individual has Attention Deficit Hyperactivity Disorder (ADHD) comprising:

providing a group of individuals a segment of which is known to have ADHD and a segment of which is known to be normal and not have ADHD;

testing each individual in the group by sampling at least one of the following physiologic measures, namely, bilateral temperature variability, heart rate, heart rate variability, muscle tension (excessive and chronic measured via surface electromyography—sEMG), bilateral muscle tension imbalance, galvanic skin response (i.e., electrodermal response—EDR), eye saccades, blood oxygen ($SpO_2$), salivary IGA, electroencephalography (EEG), peripheral blood flow (measured via photoethismosgraphy—PPG), and peripheral blood flow variability (PPG) of the individual during a pre-determined time interval when the individual is in an inactive state to provide sampled data, and analyzing the sampled data to produce a parameter value for that individual; and processing the individual parameter values for all of the members of the group to determine a threshold parameter value, which is acceptable for determining whether or not an individual has ADHD when tested by said testing.

29. A method of determining whether an individual has ADHD comprising:

sampling the peripheral skin temperature of an individual during a pre-determined time interval when the individual is in an inactive state to provide sampled peripheral skin temperature data;

dividing the data into a series of windows of equal time intervals across the pre-determined time interval;

analyzing the data using one of a Fast Fourier Transform, a wavelet transform, and a filter transform to produce a data set of values; and aggregating the data set of values for one of, less than all of, or all of the windows to produce an aggregate value which is indicative of whether or not the individual has ADHD.

* * * * *